(12) United States Patent
Tani

(10) Patent No.: US 11,779,301 B2
(45) Date of Patent: Oct. 10, 2023

(54) BLOOD FLOW PROBE, BLOOD FLOW SENSOR, AND BLOOD FLOW MEASURING INSTRUMENT

(71) Applicant: Kazuo Tani, Osaka (JP)

(72) Inventor: Kazuo Tani, Osaka (JP)

(73) Assignee: Kazuo TANI, Osaka (JP)

(*) Notice: Subject to any disclaimer, the term of this patent is extended or adjusted under 35 U.S.C. 154(b) by 351 days.

(21) Appl. No.: 17/287,507

(22) PCT Filed: Oct. 18, 2019

(86) PCT No.: PCT/JP2019/041066
§ 371 (c)(1),
(2) Date: Apr. 21, 2021

(87) PCT Pub. No.: WO2020/085233
PCT Pub. Date: Apr. 30, 2020

(65) Prior Publication Data
US 2021/0386395 A1 Dec. 16, 2021

(30) Foreign Application Priority Data
Oct. 22, 2018 (JP) .................................. 2018-198121

(51) Int. Cl.
*A61B 8/06* (2006.01)
*A61B 8/00* (2006.01)

(52) U.S. Cl.
CPC .............. *A61B 8/06* (2013.01); *A61B 8/4422* (2013.01)

(58) Field of Classification Search
CPC ........ A61B 2562/227; A61B 2562/247; A61B 5/026; A61B 5/6847; A61B 8/06; A61B 8/4422; A61B 8/4455
See application file for complete search history.

(56) References Cited

U.S. PATENT DOCUMENTS

| | | | |
|---|---|---|---|
| 2009/0240294 A1* | 9/2009 | Forsell | A61N 1/36514 128/831 |
| 2011/0066254 A1* | 3/2011 | Forsell | A61N 1/3605 600/38 |

FOREIGN PATENT DOCUMENTS

| | | |
|---|---|---|
| JP | 2915343 B2 | 7/1999 |
| JP | 2002-11007 A | 1/2002 |
| JP | 2010-264044 A | 11/2010 |
| JP | 2013-111402 A | 6/2013 |

OTHER PUBLICATIONS

PCT ISR for PCT/JP2019/041066, dated Nov. 26, 2019, 2 pages.
English translation of ISR for PCT/JP2019/04106, dated Nov. 26, 2019, 1 page.

* cited by examiner

*Primary Examiner* — Mark D Remaly
(74) *Attorney, Agent, or Firm* — Patterson Thuente IP

(57) ABSTRACT

The present invention is: a blood flow sensor that sandwiches a longitudinal-direction section of a blood vessel of a subject, from the outer circumference of such section, to generate an electrical signal corresponding to the blood flow; and a blood flow measurement instrument that processes the electrical signal from the blood flow sensor and converts the signal to an electrical signal indicating blood flow. The blood flow sensor and the blood flow measurement instrument are provided with connectors so as to be mechanically and electrically separable from each other.

16 Claims, 7 Drawing Sheets

BLOOD FLOW PROBE, BLOOD FLOW SENSOR, AND BLOOD FLOW MEASURING INSTRUMENT

CROSS-REFERENCE TO RELATED APPLICATIONS

The present application is a U.S. National Phase entry of, and claims priority to, PCT Application PCT/JP2019/041066, filed Oct. 18, 2019, which claims priority to Japanese Patent Application No. 2018-198121, filed Oct. 22, 2018, both of which are incorporated herein by reference in their entireties for all purposes.

FIELD OF THE INVENTION

The present disclosure relates to a blood flow probe configured to measure blood flow rates of a test body, such as a human body, as well as a blood flow sensor and a blood flow measuring instrument constituting the blood flow probe.

BACKGROUND OF THE INVENTION

A blood flow measuring instrument is configured to include a blood flow probe for measuring a blood flow rate through a blood vessel of a patient (test body). The blood flow measuring instrument is also configured to include a display for indicating the blood flow measured by the blood flow probe (e.g., see the official gazette of Japanese Patent No. 2915343).

A blood flow probe may measure blood flow by clamping an outer peripheral part of the blood vessel of the test body in the longitudinal direction. If such a blood flow probe is adopted, it is necessary to prepare a variety of types of flow probes for each thickness of the blood vessels. This is because a head that clamps the blood vessel differs depending on the thickness of the blood vessel.

Therefore, improved blood flow probes, blood flow sensors, and blood flow measuring instruments have been desired.

SUMMARY OF THE INVENTION

A first aspect of the present disclosure is a blood flow probe configured to measure a blood flow rate through a blood vessel of a test body and to convert the measured blood flow rate into an electric signal. The blood flow probe includes a blood flow sensor configured to generate an electric signal in accordance with the blood flow rate by clamping a part of the blood vessel of the test body in the longitudinal direction from its outer periphery of the blood vessel. The blood flow probe also includes a blood flow measuring instrument configured to process the electric signal from the blood flow sensor and to convert to the electric signal into a value representing the blood flow rate. The blood flow sensor and the blood flow measuring instrument include a connector configured to connect the blood flow sensor to the blood flow measuring instrument, so as to be mechanically and electrically disconnectable from each other. The blood flow sensor can be selected from various types having different sizes, so as to correspond to various thicknesses of the blood vessels. The selected blood flow sensor can be connected to the common blood flow measuring instrument via the connector, regardless of its size.

According to the first aspect of the present disclosure, the blood flow probe is configured by separably connecting the blood flow sensor and the blood flow measuring instrument. Therefore, the blood flow instrument is commonly made so that the blood flow sensor can be replaced as needed. It is thus possible to make the blood flow sensor disposable, so that cleansing and sterilization work of the blood flow sensor, which requires cleansing and sterilization after each use, can be eliminated. In addition, the blood flow measuring instrument can be commonly used by replacing the blood flow sensor to correspond to the blood vessel size of the test body.

A second aspect of the present disclosure is a blood flow sensor used for a blood flow probe. The blood flow sensor is configured to generate an electric signal in accordance with the blood flow rate by clamping a part of the blood vessel of the test body in the longitudinal direction from its outer periphery of the blood vessel. The blood flow measuring instrument configured to process the electric signal from the blood flow sensor and to convert the electric signal onto a value representing the blood flow rate. The blood flow sensor is connected to the blood flow measuring instrument via a connector, so as to be mechanically and electrically disconnectable. The blood flow sensor can also be selected from various different sizes, so as to correspond to the various thicknesses of the blood vessels. The selected blood flow sensor can be connected to the common blood flow measuring instrument via the connector, regardless of the size of the blood flow sensor.

According to the second aspect of the present disclosure, the blood flow probe is configured by separably connecting the blood flow sensor to the blood flow measuring instrument. Therefore, the blood flow instrument can be commonly made, so that the blood flow sensor can be replaced as needed when being used as a blood flow probe. It is thus possible to make the blood flow sensor disposable, so that cleansing and sterilization of the blood flow sensor, which requires cleansing and sterilization after use, can be eliminated. In addition, the blood flow measuring instrument can be commonly used by replacing the blood flow sensor according to the blood vessel size of the test body.

A third aspect of the present disclosure is a blood flow measuring instrument used for a blood flow probe including a blood flow sensor. The blood flow sensor is configured to generate an electric signal in accordance with the blood flow rate, by clamping a part of the blood vessel of the test body in the longitudinal direction from the outer periphery of the blood vessel. The blood flow probe also includes a blood flow measuring instrument configured to process the electric signal from the blood flow sensor and to convert to the electric signal into a value representing the blood flow rate. The blood flow measuring instrument is connected to the blood flow sensor via a connector, so as to be mechanically and electrically disconnectable. The blood flow sensor can be selected from various different sizes, so as to correspond to various thicknesses of the blood vessels. The selected blood flow sensor can be connected to the common blood flow measuring instrument via the connector, regardless of its size.

According to the third aspect of the present disclosure, the blood flow probe is configured by separably connecting the blood flow sensor to the blood flow measuring instrument. Therefore, the blood flow instrument is commonly made, so that the blood flow sensor can be replaced as needed when used as a blood flow probe. It is thus possible to make the blood flow sensor disposable, so that cleansing and sterilization work of the blood flow sensor, which requires cleansing and sterilization after each use, can be eliminated. In addition, the blood flow measuring instrument can be commonly used by replacing the blood flow sensor based on the blood vessel size of the test body.

A fourth aspect of the present disclosure is a blood flow sensor used for a blood flow probe. The blood flow sensor is configured to generate electric signals in accordance with the blood flow rate by clamping a part of the blood vessel of the test body in the longitudinal direction from the outer periphery of the blood vessel. The blood flow probe also includes a blood flow measuring instrument configured to process the electric signal from the blood flow sensor and to convert to the electric signal into a value representing the blood flow rate. The blood flow sensor includes a reflector which is connected to the blood flow measuring instrument via a connector, so as to be mechanically and electrically disconnectable. The reflector is configured to reflect received ultrasonic waves while being placed on the outer periphery of the blood vessel of a test body. A first transducer is configured to transmit ultrasonic waves from the opposite side of the reflector toward the reflector and to receive the ultrasonic waves reflected by the reflector, while the blood vessel of the test body is clamped therebetween. A second transducer is positioned side by side with the first transducer on the opposite side of the reflector. The second transducer is configured to transmit ultrasonic waves to be reflected by the reflector and toward the first transducer and to receive the ultrasonic waves reflected by the reflector and transmitted by the first transducer, all while the blood vessel of the test body is clamped between the reflector and the second transducer. The distance between the reflector and the first and second transducers can be changed in accordance with the thickness of the blood vessel to be clamped between the first and second transducers and the reflector. The first and second transducers have an angle changing mechanism configured to change the ultrasonic wave transmission/reception angle according to their distance from the reflector, so that the ultrasonic waves transmitted from the first or second transducer are reflected by the reflector and received by the corresponding second or first transducer, regardless of the change in distance from the reflector.

A fifth aspect of the present disclosure is a blood flow probe configured to measure a blood flow rate through a blood vessel of a test body and to convert the measured blood flow rate into an electric signal. The blood flow probe includes a blood flow sensor configured to generate an electric signal in accordance with the blood flow rate, by clamping a part of the blood vessel of the test body in the longitudinal direction from its outer periphery. The blood flow probe also includes a blood flow measuring instrument configured to process the electric signal from the blood flow sensor and to convert to the electric signal into a value representing the blood flow rate. The blood flow sensor and the blood flow measuring instrument respectively include a connector for mechanically and electrically connecting the blood flow sensor and the blood flow measuring instrument, so as to be disconnectable from each other. The blood flow sensor serves as the blood flow sensor as described in the above fourth aspect.

According to the fourth and fifth aspects of the present disclosure, the reflector is arranged to face the first and second transducers with the blood vessel interposed therebetween and is movable in accordance with the thickness of the blood vessel. At the same time, the transmission/reception angles of the ultrasonic waves by the first and second transducers may be changed in accordance with the movement of the reflector. Therefore, by moving the reflector in accordance with the thickness of the blood vessel, it is possible to measure the blood flow rate through the blood vessel with only one blood flow probe, despite the thicknesses of the blood vessel.

A sixth aspect of the present disclosure is the blood flow measuring instrument according to the third aspect, wherein the blood flow measuring instrument includes an exterior that can withstand a predetermined sterilization process. The exterior can have at least one of airtightness and watertightness that can withstand the predetermined sterilization process.

According to the sixth aspect of the present disclosure, since the blood flow measuring instrument is configured to withstand sterilization processing, it can be sterilized so as to be repeatedly used.

A seventh aspect of the present disclosure is the blood flow probe according to the first or fifth aspect, the blood flow probe further including a sterilization bag configured to cover the blood flow measuring instrument while the blood flow sensor and the blood flow measuring instrument are connected.

According to the seventh aspect of the present disclosure, the blood flow measuring instrument is covered with a sterilization bag while the blood flow sensor is connected to the blood flow measuring instrument. Therefore, while the blood flow sensor may need to be sterilized or replaced with a new one, the blood flow measuring instrument can be maintained in a sterilized state by using the sterilization bag. The blood flow measuring instrument can therefore be used as a blood flow probe in the sterile state, even if the blood flow measuring instrument is not fully sterile.

An eighth aspect of the present disclosure is the blood flow probe according to the first, fifth, or seventh aspect, in that the blood flow sensor and the blood flow measuring instrument are connected via an extension cable that mechanically and electrically maintains the connected state despite the blood flow sensor and the blood flow measuring instrument being separated from each other.

According to the eighth aspect of the present disclosure, when an extended blood flow probe is needed, an extension cable may be connected between the blood flow measuring instrument and the blood flow sensor to extend the length of the blood flow probe.

DETAILED DESCRIPTION OF THE DRAWINGS

Structure of First Embodiment

Figure 1:
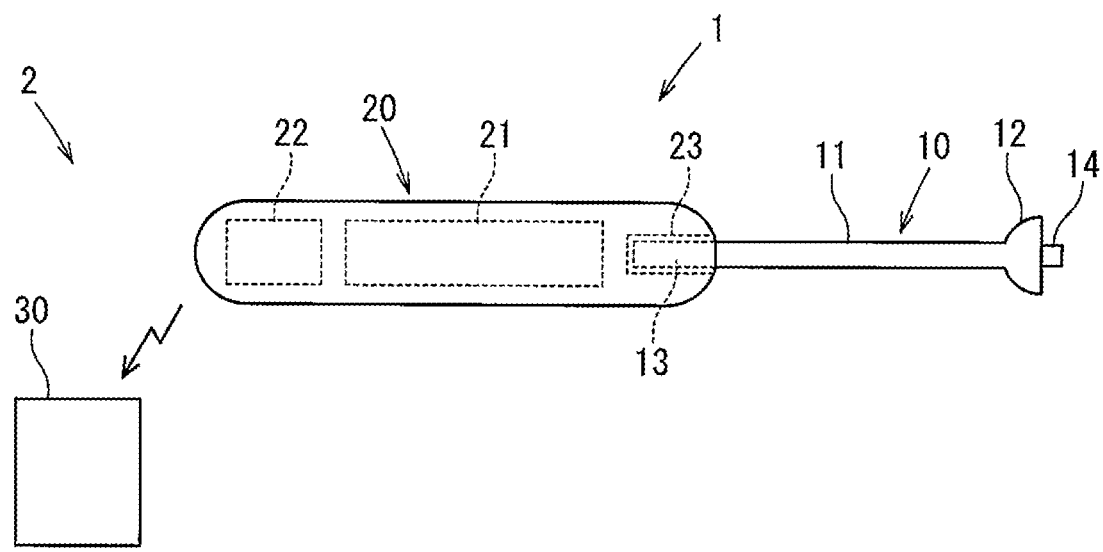
FIG. 1 is a schematic structural view of a blood flow probe according to a first embodiment of the present disclosure.
Figure 2:
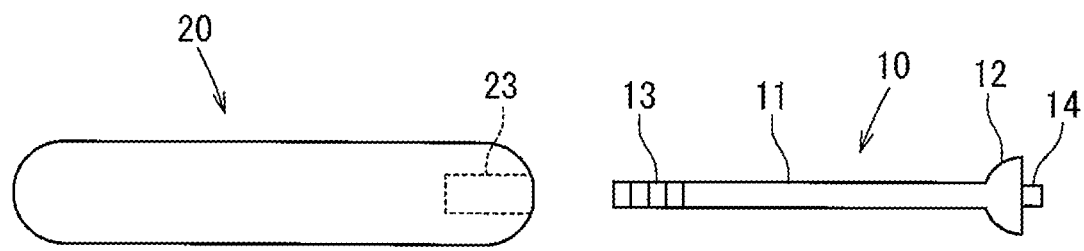
FIG. 2 is a schematic structural view illustrating a state in that the blood flow probe of FIG. 1 is separated into a blood flow measuring instrument and a blood flow sensor.

FIGS. 1 and 2 show a first embodiment of the present disclosure. The first embodiment is, for example, a blood flow probe 1 configured to measure a blood flow rate through a blood vessel of a patient (test body) during an operation. The blood flow probe 1 is also configured to convert a measured blood flow rate into an electric signal. As shown in FIG. 1, the blood flow measuring instrument 2 is configured such that the blood flow probe 1 wirelessly transmits the measured blood flow rate to a display 30. The display 30 indicates the measured blood flow rate to the doctor performing the operation.

The blood flow probe 1 includes a blood flow sensor 10 and a blood flow measuring instrument 20 that are separably connected to each other. A male connector 13 of the blood flow sensor 10 and a female connector 23 of the blood flow measuring instrument 20 are coupled to each other to establish a mechanical and electrical connection between the blood flow sensor 10 and the blood flow measuring instrument 20. The connectors 13, 23 for separably connecting the blood flow sensor 10 and the blood flow measuring instrument 20 are not limited to those having structures shown in FIGS. 1 and 2, and various other known types may be adopted.

Figure 12:
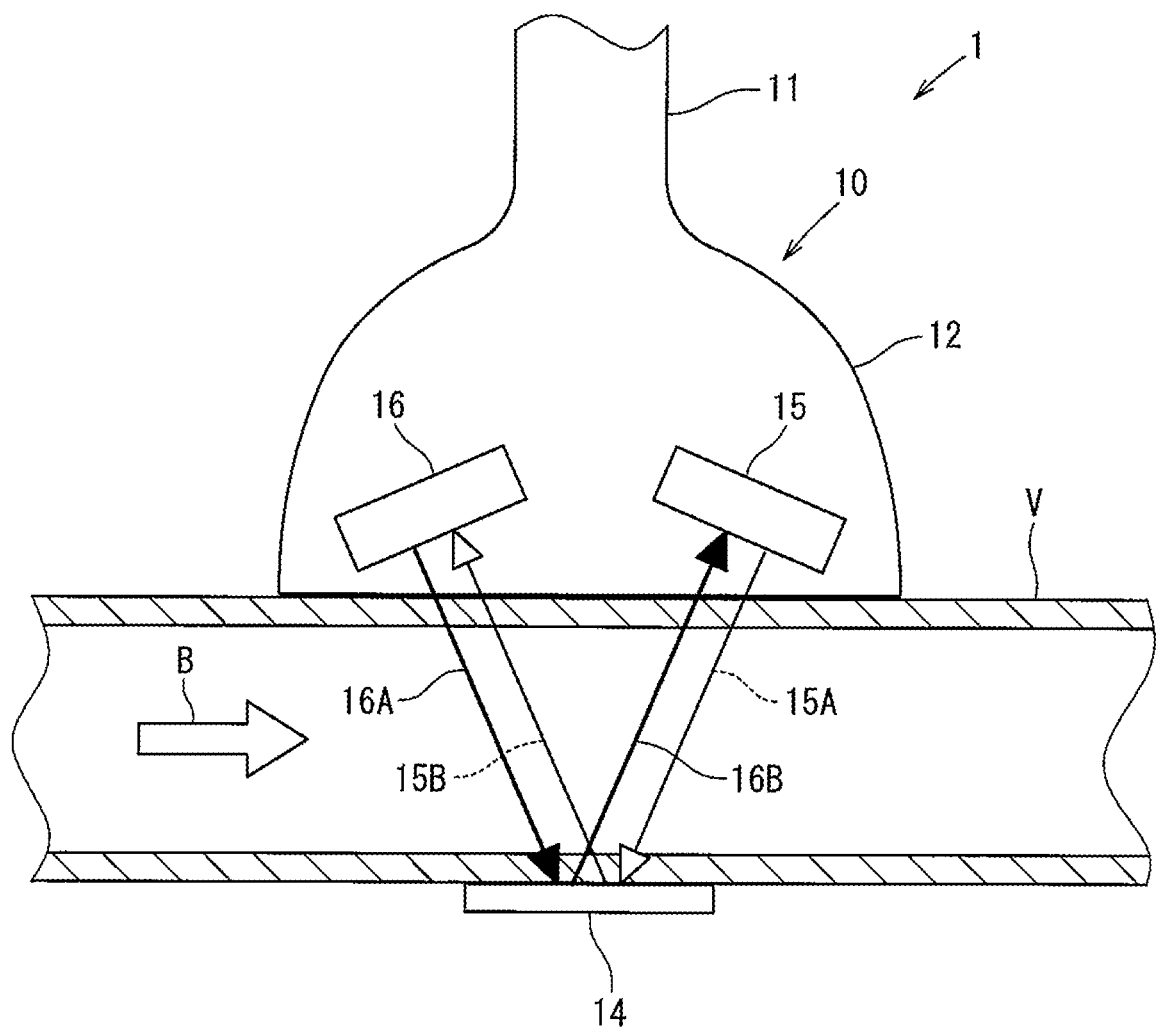
FIG. 12 is an explanatory view illustrating a blood flow measuring condition of the blood flow probe.

As shown in FIG. 12, the blood flow probe 1 is a known transit time type blood flow probe. This type of probe includes first and second transducers 15, 16 built in a head 12 of a blood flow sensor 10, so as to oppose to a reflector 14 at a front end. The ultrasonic waves 15A, 16A are respectively transmitted by the first and second transducers 15, 16. These ultrasonic waves 15A, 16A are reflected by the reflector 14, while a blood vessel V is clamped between the reflector 14 and the first and second transducers 15, 16. The reflected ultrasonic waves 15B, 16B are received by the first and second transducers 15, 16, on the non-transmitted side. The blood flow probe 1 measures the flow rate of the blood flow B flowing through the blood vessel V based on the time difference required to receive the transmitted ultrasonic waves by the first and second transducers 15, 16.

As shown in FIG. 1, the blood flow measuring instrument 20 includes a measuring circuit 21. The measuring circuit 21 exchanges electric signals between the first and second transducers 15, 16 within the head 12 of the blood flow sensor 10 via each of the connectors 23, 13. Therefore, a rod 11 of the blood flow sensor 10 includes an electric circuit (not shown) for transmitting operation signals from the measuring circuit 21 to the first and second transducers 15, 16. The rod 11 also includes an electric circuit (not shown) for transmitting received signals of the transducers 15, 16 by the measuring circuit 21. The measuring circuit 21 is configured to measure the flow rate of the blood flow B flowing through the blood vessel V based on the time difference required to receive the transmitted ultrasonic waves by the first and second transducers 15, 16, as described above. The rod 11 is preferably bendable so that the head 12 can be easily attached to blood vessels at various angles.

As shown in FIG. 1, the blood flow measuring instrument 20 includes a transmitter 22 configured to wirelessly transmit the blood flow rate measured by the measuring circuit 21 to the display 30. Since this wireless communication is performed in an operating room, short-range communication, such as Bluetooth (registered trademark), may be adopted. Although not shown, a battery or batteries for supplying power to the measuring circuit 21 and the transmitter 22 is/are provided within the blood flow measuring instrument 20.

Detailed Structure of Head 12

Figure 3:
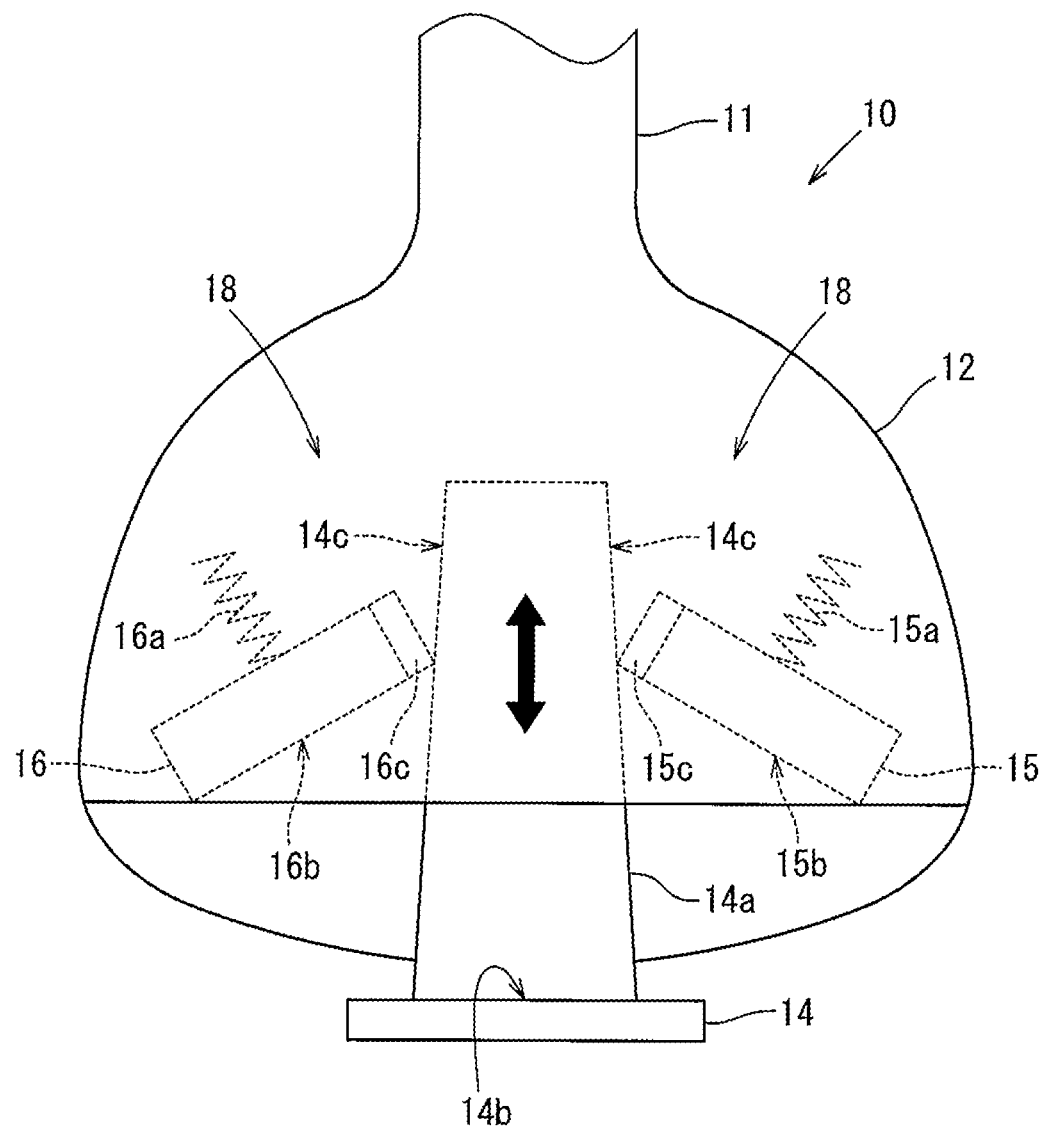
FIG. 3 is an enlarged front view illustrating a front end of the blood flow sensor.
Figure 4:
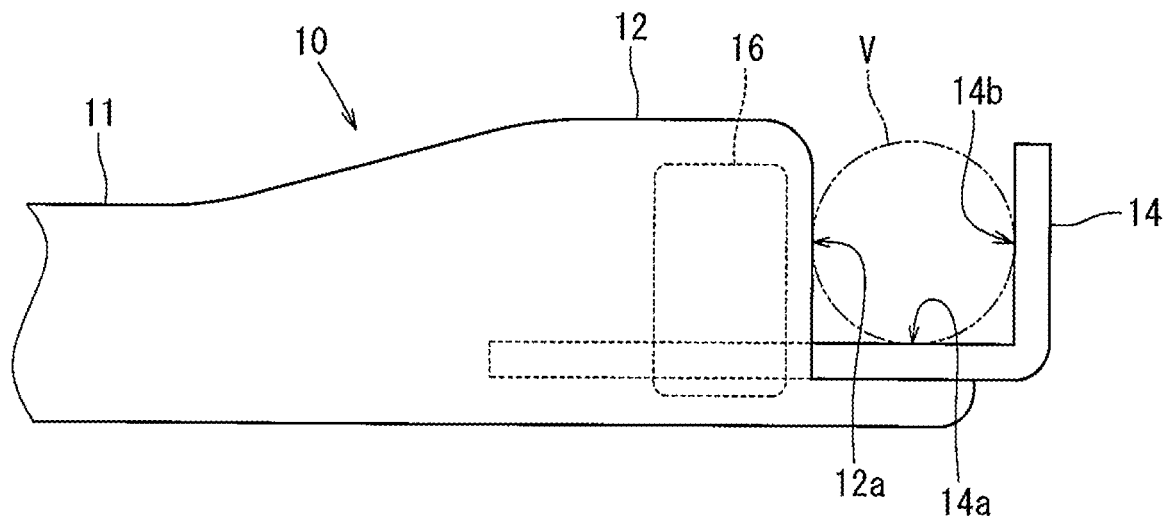
FIG. 4 is an enlarged side view illustrating a front end of the blood flow sensor.

As shown in FIGS. 3 and 4, a reflector 14 is coupled to the front end of the head 12, so as to freely project and retract by a plate-shaped stem 14a, as indicated by an arrow in FIG. 3. In this embodiment, the reflector 14 and the stem 14a are integrally formed. In FIG. 3, an upper surface of the reflector 14 serves as an ultrasonic wave reflecting surface 14b. Further, as shown in FIG. 3, the stem 14a has a trapezoidal shape, in which the plate width narrows toward the inside of the head 12. Further, the stem 14a is pressed against the inner wall (not shown) of the head 12 in up-and-down direction in FIG. 4. The head 12 applies an appropriate frictional resistance to the stem 14a during a projecting and retracting motion.

As shown in FIG. 3, the first and second transducers 15, 16 are provided with the sliding portions 15c, 16c at each end. The sliding portions 15c, 16c are allowed to come in contact with sliding surfaces 14c located on both sides of the stem 14a. Oscillating surfaces 15b, 16b of the first and second transducers 15, 16 are arranged so as to be oriented toward the reflecting surface 14b of the reflector 14. The first and second transducers 15, 16 are provided with compression springs 15a, 16a on sides opposite of each of the respective oscillating surfaces 15b, 16b. Each of the sliding portions 15c, 16c is made to always come in contact with the corresponding sliding surface 14c of the stem 14a, due to the biasing force of the compression springs 15a, 16a.

Therefore, the blood flow rate through various blood vessel V can be measured, as the front end of the stem 14a is operable to project from and retract in the head 12 to accommodate differences in the thickness of the various blood vessel to be clamped between the reflector 14 and the first and second transducers 15, 16. That is, as shown in FIG. 4, independent of the thickness of the blood vessel V, the outer peripheral surface of the blood vessel V may be contacted at three locations and be clamped. For instance, the outer peripheral surface of the blood vessel V may be in contact with a front end face 12a of the head 12, the reflecting surface 14b of the reflector 14, and the stem 14a of the reflector 14, and be clamped therebetween.

As described above, when the front end of the stem 14a is operated so as to project from and retract in the head 12, the angles of the first and second transducers 15, 16 change in accordance with the sliding positions of the sliding surface 14c of the stem 14a and the sliding portions 15c, 16c of the first and second transducers 15, 16. Therefore, the oscillating surfaces 15b, 16b of the first and second transducers 15, 16 are always oriented toward the reflecting surface 14b of the reflector 14, regardless of the change in positions of the reflector 14. That is, the ultrasonic transmission/reception angles of the first and second transducers 15, 16 are changed in accordance with the positions of the reflector 14. Therefore, the sliding surface 14c of the stem 14a and the sliding portions 15c, 16c of the first and second transducers 15, 16 may be part of an angle changing mechanism 18.

In the first embodiment, the stop position of the stem 14a, with respect to the head 12, is configured to be held by the frictional resistance between the stem 14a and the inner wall of the head 12. However, one or more sliding surface 14c of the stem 14a may be formed as an uneven surface (not shown) that protrudes and recesses in the protruding and retracting direction of the stem 14a. This may provide a sense of moderation to the motion and stop of the stem 14a, as these uneven surfaces engage the sliding portions 15c, 16c of the first and second transducers 15, 16. Alternatively, a rotary shaft (not shown) may be coupled to the sliding surface 14c of the stem 14a, so as to allow the stem 14a to move with respect to the head 12 by operating the rotary shaft to rotate. Furthermore, in order to easily determine the moved amount of the stem 14a with respect to the head 12, a scale (not shown) may be provided on the exposed surface of the stem 14a, or, a scale (not shown) may be provided on the surface of the head 12 such that a pointer (not shown) moving together with the stem 14a indicates the scale.

Operation and Effect of First Embodiment

According to the first embodiment, the blood flow sensor 10 and the blood flow measuring instrument 20 are separably connected by the male connector 13 and the female connector 23, so as to constitute the blood flow probe 1. Therefore, the blood flow sensor 10 can be independently replaced as needed while using the common blood flow measuring instrument 20. Therefore, the blood flow sensor 10 can be made to be disposable, so that cleansing and sterilization work of the blood flow sensor 10, which requires cleansing and sterilization after use, can be eliminated. Further, the blood flow measuring instrument 20 may be commonly used by replacing the blood flow sensor 10 according to the blood vessel size of the test body. If the blood flow measuring instrument 20 is repeatedly used after the blood flow sensor 10 is replaced, the blood flow measuring instrument 20 needs to be sterilized. Therefore, the blood flow measuring instrument 20 is configured to have an exterior (particularly, the material of the exterior) that can withstand a sterilization process and that can have at least one of airtightness or watertightness capable of withstanding the predetermined sterilization process.

Further, according to the first embodiment, the reflector 14 is arranged to face the first and second transducers 15, 16 with the blood vessel V interposed therebetween. The reflector 14 is made to be movable according to the thickness of the blood vessel V to be tested. At the same time, the first and second transducers 15, 16 are configured such that orientations of their oscillating surfaces 15b, 16b can vary in response to the movement of the reflector 14. That is, the oscillating surfaces 15b, 16b are configured to always be oriented toward the reflecting surface 14b of the reflector 14, despite the movement of the reflecting surface 14b. Therefore, by moving the reflector 14 to accommodate the thickness of the blood vessel V, it is possible to measure the blood flow rate through blood vessels V having different thicknesses with one blood flow probe 1.

Table 1 shows an example in which the blood flow sensor 10 is classified into four types, types I to IV. Each type of blood flow sensor 10 being classified into the four types is determined by setting a size range of blood vessels V that can be clamped by the reflector 14 of the head 12, each based on a predetermined range (1.0 to 4.5 mm, 3.9 to 7.5 mm, 6.9 to 14.0 mm, and 13.0 to 35.0 mm). Alternatively, a blood vessel V of almost any size (for example, 1.0 to 40.0 mm) may be clamped by the reflector 14 of the head 12 with only one type of blood flow sensor 10.

TABLE 1

| Types | Measuring Ranges |
|---|---|
| I | 1.0~4.5 mm |
| II | 3.9~7.5 mm |
| III | 6.9~14.0 mm |
| IV | 13.0~35.0 mm |

As shown in Table 1, it is possible to significantly reduce the number of the types of the blood flow sensor 10, for instance by preparing the blood flow sensor 10 in only four different types, as compared to the case where the reflector 14 is not movable because it is fixed to the head 12 (which would require the blood flow sensor 10 to be prepared for each size). Moreover, since the blood flow sensor 10 is classified into four different types, the amount of movement of the reflector 14 needed to match the size of the blood vessel V can be made smaller, as compared to the case where they are not classified in different types. Therefore, an angle changing mechanism 18 configured to change the angle(s) of the first and second transducers 15, 16 in accordance with the movement of the stem 14a can be reduced in size, as compared to the case where the reflector 14 is greatly moved in order to match blood vessels V of almost any sizes. As a result, the size of the head 12 can be reduced.

Second Embodiment

Figure 5:
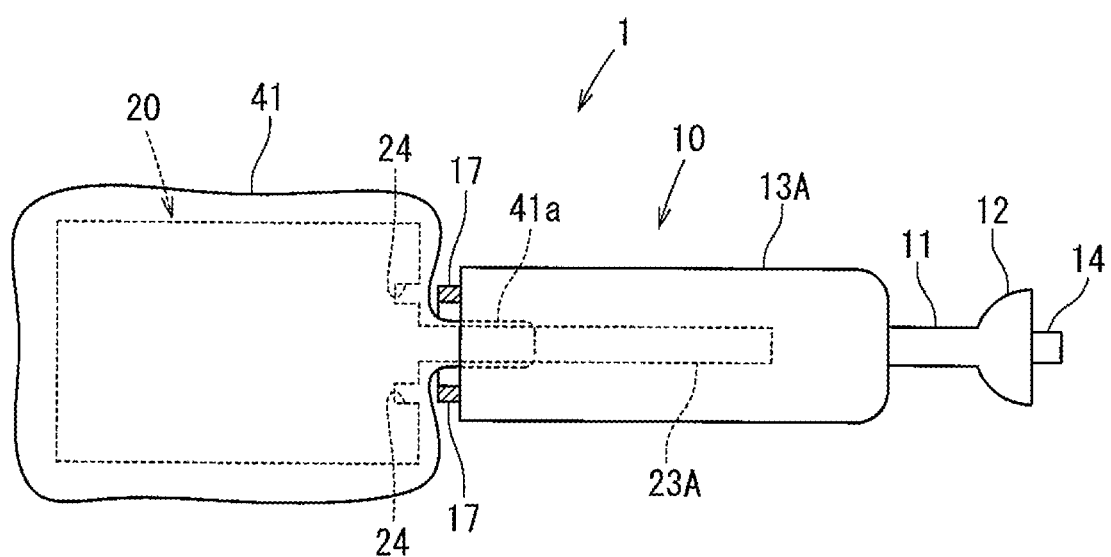
FIG. 5 is a schematic structural view of a blood flow probe according to a second embodiment of the present disclosure.

FIG. 5 shows a second embodiment of the present disclosure. The second embodiment is characterized in that the blood flow measuring instrument 20 is covered with a sterilized bag 41, in contrast to the first embodiment. Further, in the second embodiment, among the connectors that selectively connect the blood flow sensor 10 and the blood flow measuring instrument 20, the male connector 23A is provided in the blood flow measuring instrument 20 and the female connector 13A is provided in the blood flow measuring sensor 10. The rest of the structure is basically the same as that of the first embodiment. Accordingly, a description of the substantially identical structures will not be repeated.

The blood flow measuring instrument 20 is entirely covered with the sterilized bag 41. An opening 41a of the sterilization bag 41 is coupled with a projecting part of the male connector 23A, the projecting part formed to project from the blood flow measuring instrument 20. As a result, the outside of the sterilized bag 41 is sterile, even if the blood flow measuring instrument 20 is not sterile. A bag that can withstand gas sterilization, electron beam sterilization, high-pressure steam sterilization, gamma ray sterilization, etc. may be used as the sterilization bag 41.

When the male connector 23A and the female connector 13A are coupled, a protrusion 17 is formed at an end of the female connector 13A so as to protrude toward the blood flow measuring instrument 20 (in FIG. 5, the protrusion 17 is illustrated in cross-section). The end of the female connector 13A is arranged to face the blood flow measuring instrument 20. Further, a fitting hole 24 for receiving and fitting the protrusion 17 is formed on the surface of the blood flow measuring instrument 20 facing the protrusion 17. The fitting hole 24 is formed in an annular shape, so as to be enclosed around the male connector 23A. The protrusion 17 is also formed in an annular shape, corresponding to the fitting hole 24. Therefore, when the male connector 23A and the female connector 13A are coupled and the blood flow sensor 10 and the blood flow measuring instrument 20 are connected, the projection 17 is fitted into the fitting hole 24, with the sterilized bag 41 interposed therebetween. The opening 41a of the sterilized bag 41 is then interposed between the protrusion 17 and the fitting hole 24, such that the blood flow measuring instrument 20 is sealed in the sterilized bag 41.

According to the second embodiment, the blood flow measuring instrument 20 is covered with the sterilized bag 41 while the blood flow measuring sensor 10 is connected to the blood flow measuring instrument 20. Therefore, while the blood flow sensor 10 can be sterilized or replaced with a new one, the blood flow measuring instrument 20 can be maintained to be sterile due to the sterilized bag 41. Accordingly, the blood flow probe 1 can be used in a sterile state, even if the blood flow measuring instrument 20 has not been fully sterilized.

Third Embodiment

Figure 6:
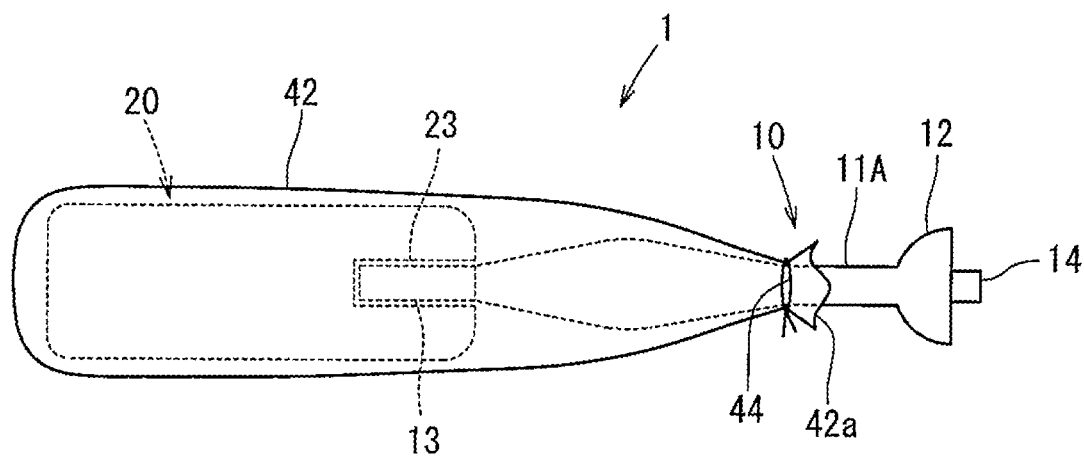
FIG. 6 is a schematic structural view of a blood flow probe according to a third embodiment of the present disclosure.

FIG. 6 shows a third embodiment of the present disclosure. The third embodiment is characterized in that a manner of covering the blood flow measuring instrument 20 with a sterilized bag 42 is changed with regard to the second embodiment (see FIG. 5). Specifically, the entire blood flow measuring instrument 20, including the male connector 13 and the female connector 23, is covered with a sterilization bag 42. Therefore, the opening 42a of the sterilization bag 42 is sealed by a string 44 on the rod 11A of the blood flow sensor 10. The rod 11A is formed such that its outer diameter on the side of the male connector 13 gradually increases. Accordingly, the opening 42a of the sterilization bag 42 is not easily removed toward the side of the male connector 13 of the rod 11A. The rest of the structure is basically the same as that of the first embodiment, and thus the substantially identical structures will not be repeatedly described.

In the third embodiment, similar to the second embodiment, while the blood flow sensor 10 may be sterilized or replaced with a new one, the blood flow measuring instrument 20 can be maintained to be sterile by the sterilization bag 42. Accordingly, the blood flow probe 1 can be used in a sterile state, even if the blood flow measuring instrument 20 has not been fully sterilized.

Use of Extension Cable 50 (First Embodiment)

Figure 7:
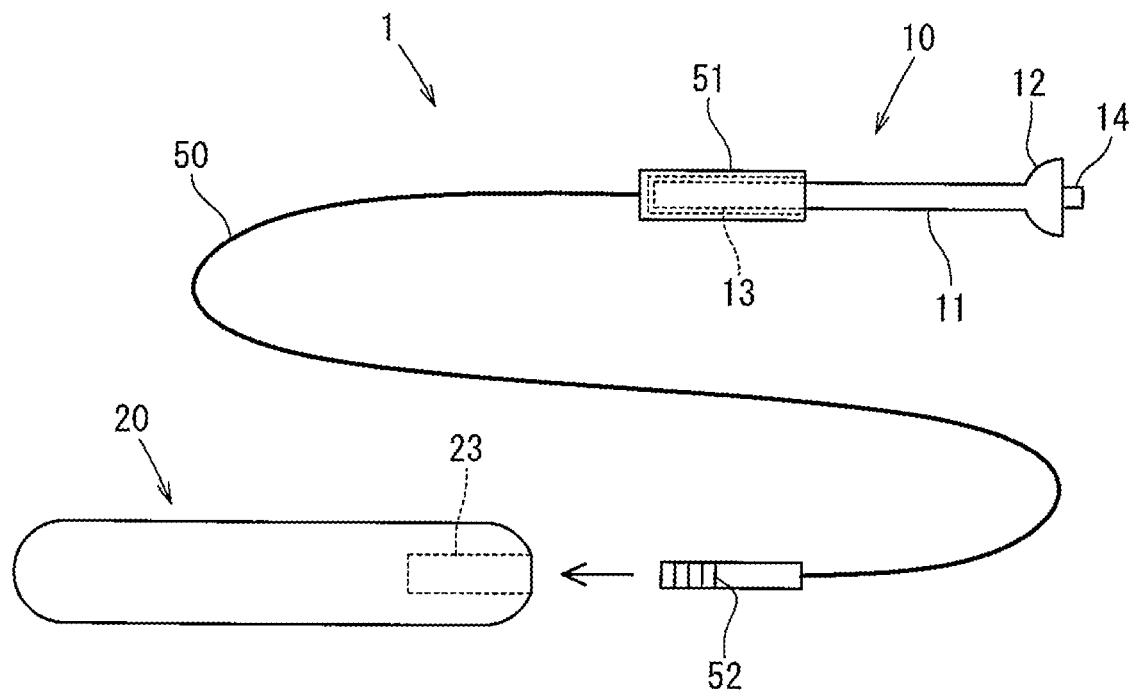
FIG. 7 is a schematic structural view illustrating a state in which an extension cable is being connected between the blood flow measuring instrument and the blood flow sensor according to the first embodiment.

FIG. 7 shows a case where an extension cable 50 is connected and used between the blood flow sensor 10 and the blood flow measuring instrument 20 of the first embodiment. The extension cable 50 is provided with electric wiring (not shown), similar to that provided in the rod 11 of the blood flow sensor 10. That is, the extension cable 50 is provided with an electric circuit for transmitting operation signals from the measuring circuit 21 of the blood flow measuring instrument 20 to the first and second transducers 15, 16 of the blood flow sensor 10 (see FIGS. 1 and 3). The extension cable 50 is also provided with an electric circuit for transmitting the signals received by the first and second transducers 15, 16 to the measuring circuit 21 (see FIGS. 1 and 3).

A female connector 51, which can be mechanically and electrically connected to the male connector 13 of the blood flow sensor 10, is coupled to one end of the extension cable 50. Further, a male connector 52, which can be mechanically and electrically connected to the female connector 23 of the blood flow measuring instrument 20, is coupled to the other end of the extension cable 50. The extension cable 50 is formed to be bendable and can be set to any length. In this case, the female connectors 51, 23 are the same size, and the male connectors 52, 13 are the same size. Therefore, when the extension cable 50 is not being used, the male connector 13 and the female connector 23 can be mechanically and electrically connected.

When a long blood flow probe 1 is required, the desired length can be achieved by connecting the extension cable 50 between the blood flow sensor 10 and the blood flow measuring instrument 20, as described above. For example, the blood flow measuring instrument 20 can be supported on a part of an operation table while the blood flow sensor 10 is attached to a blood vessel of a patient undergoing an operation. The blood flow measuring instrument 20 can be connected to the blood flow sensor 10 via the extension cable 50. Further, it is possible to allow the blood flow measuring instrument 20 to be easily supported, for example, by an operation table by providing a clip integral to the blood flow measuring instrument 20.

Fourth Embodiment

Figure 8:
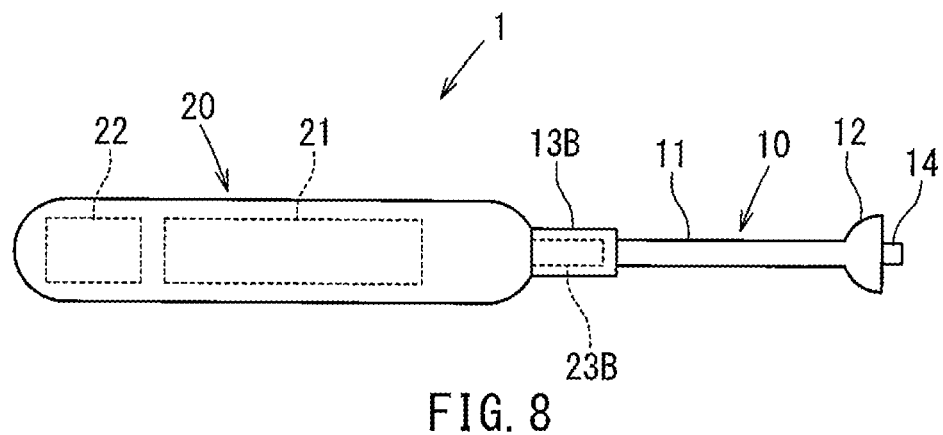
FIG. 8 is a schematic structural view of a blood flow probe according to a fourth embodiment of the present disclosure.
Figure 9:
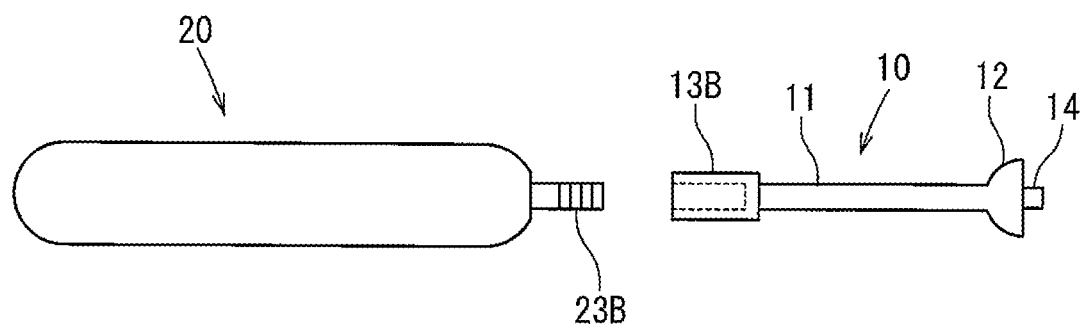
FIG. 9 is a schematic structural view illustrating a state in which the blood flow probe of FIG. 8 is separated into a blood flow measuring instrument and the blood flow sensor.

FIGS. 8 and 9 show a fourth embodiment of the present disclosure. The fourth embodiment is characterized in that the male-female relationship of the connector that connects the blood flow sensor 10 and the blood flow measuring instrument 20 is reversed from that of the first embodiment (see FIG. 1). Specifically, a female connector 13B is provided at the front end of the rod 11 of the blood flow sensor 10, and a male connector 23B is provided at the front end of the blood flow measuring instrument 20. As shown in FIG. 8, while the male connector 23B is inserted into and coupled to the female connector 13B, the blood flow sensor 10 and the blood flow measuring instrument 20 are mechanically coupled. At the same time, a measuring circuit 21 of the blood flow instrument 20 is electrically connected to an electric circuit in the rod 11. The rest of the structures are basically the same as those of the first embodiment, and thus the substantially identical structures will not be repeatedly described.

The fourth embodiment differs from the first embodiment only in that the male-female relationship of the connectors is reversed, and may achieve the same operation and effect as the first embodiment.

Fifth Embodiment

Figure 10:
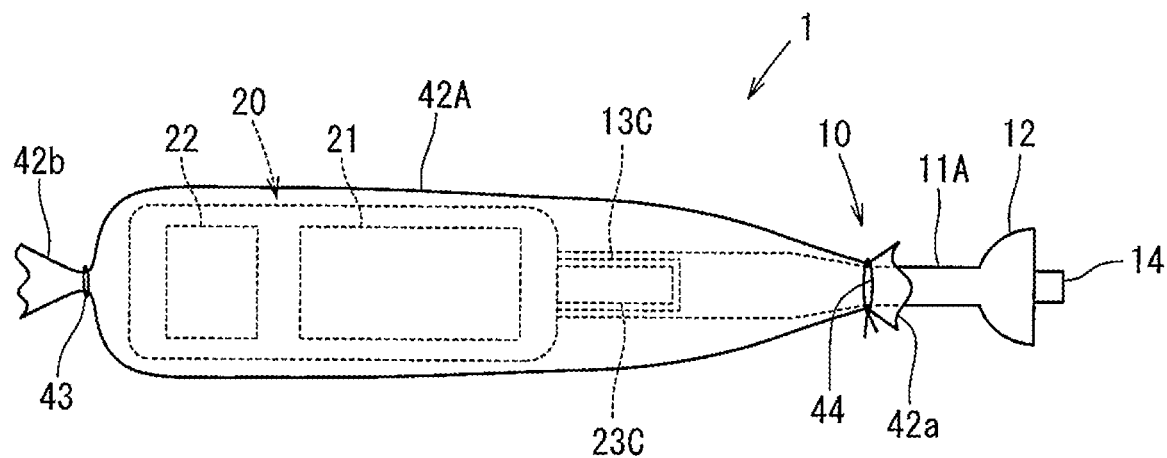
FIG. 10 is a schematic structural view of a blood flow probe according to a fifth embodiment of the present disclosure.

FIG. 10 shows a fifth embodiment of the present disclosure. The fifth embodiment is characterized in that the male-female relationship of the connector for connecting the blood flow sensor 10 and the blood flow measuring instrument 20 is reversed from that of the third embodiment (see FIG. 6). Further, the sterilized bag 42A is made open at both ends. One opening 42a of the sterilized bag 42A is tied with a string 44, so as to come in close contact with the surface of the rod 11A. At the same time, the other opening 42b is sealed with a string 43. The rest of the structures are basically the same as those of the third embodiment, and thus the substantially identical structures will not be repeatedly described.

Specifically, a female connector 13C is provided at the front end of the rod 11A of the blood flow sensor 10, and a male connector 23C is provided at the front end of the blood flow measuring instrument 20. While the male connector 23C is inserted into and coupled to the female connector 13C, the blood flow sensor 10 and the blood flow measuring instrument 20 are mechanically coupled. At the same time, a measuring circuit 21 of the blood flow instrument 20 is electrically connected to an electric circuit in the rod 11A.

The fifth embodiment differs from the third embodiment in that the male-female relationship of the connector is reversed and the manner of sealing the sterilized bag 42A is different. However, the same operation and effect as the third embodiment may be achieved.

Use of Extension Cable 50 (Fourth Embodiment)

Figure 11:
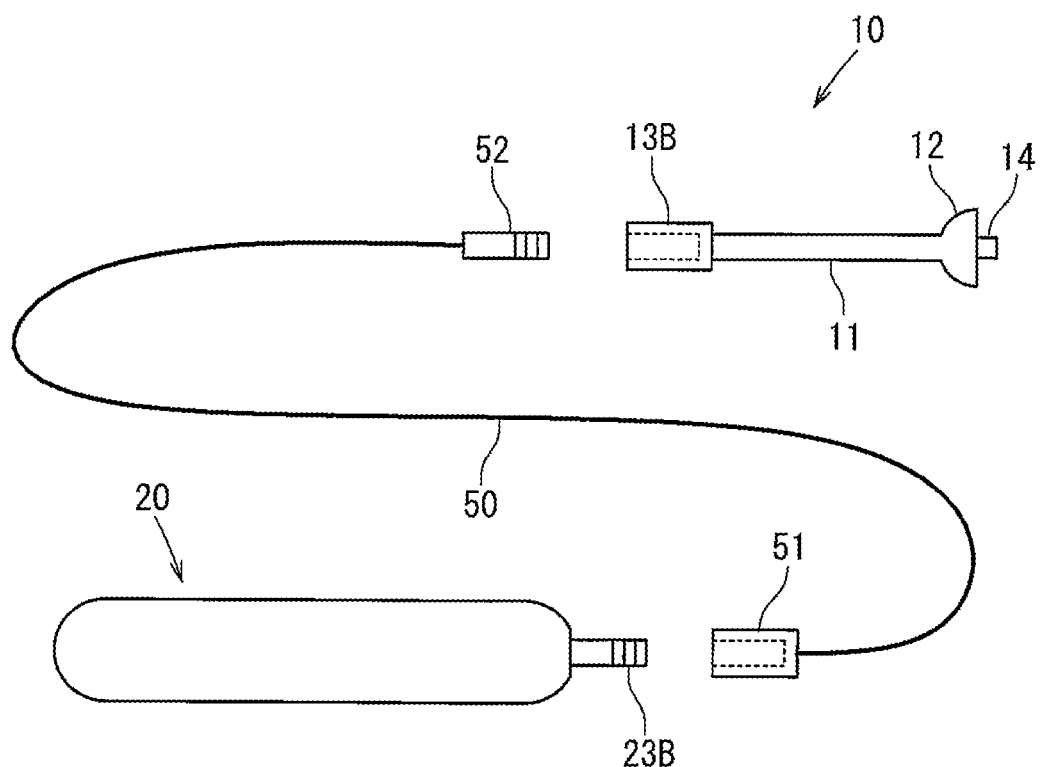
FIG. 11 is a schematic structural view illustrating a state in which an extension cable is being connected between the blood flow measuring instrument and the blood flow sensor.

FIG. 11 shows a case where an extension cable 50 is used to connect the blood flow sensor 10 and the blood flow measuring instrument 20 of the fourth embodiment (see FIGS. 8 and 9). The extension cable 50 is essentially the same as that in FIG. 7, except that the male and female relations of the connectors connected at both ends of the extension cable 50 are opposite to those of FIG. 7. The rest of the structures are essentially the same as those of FIG. 7.

A male connector 52, which is configured to be mechanically and electrically connected to the female connector 13B of the blood flow sensor 10, is coupled to one end of the extension cable 50. A female connector 51, which is configured to be mechanically and electrically connected to the male connector 23B of the blood flow measuring instrument 20, is coupled to the other end of the extension cable 50. The extension cable 50 is formed to be bendable and can be set to any length. In this case, the female connectors 51, 13B are the same size, and the male connectors 52, 23B are the same size. Therefore, when the extension cable 50 is not being used, the male connector 23B and the female connector 13B can be mechanically and electrically connected.

When a long blood flow probe 1 is required, this can be achieved by connecting an extension cable 50 between the blood flow sensor 10 and the blood flow measuring instrument 20, as described above.

Other Embodiments

Although specific embodiments have been described above, the present disclosure shall not be limited to those structures and configurations, and various modifications, additions, and deletions are possible. For example, the blood flow probe of the present disclosure can be applied not only to the human body, but also to the blood vessels of other animals. Further, it can be applied not only to the blood vessels of the heart, but also to other organs and blood vessels in the body.

In the above embodiment, the blood flow probe is of the transit time type, but it may also be of any other measurement method type known to the public.

The invention claimed is:

1. A blood flow probe configured to measure a blood flow rate through a blood vessel of a test body and to convert the measured blood flow rate into an electric signal, comprising:
 a blood flow sensor configured to generate and receive ultrasonic waves and to generate electric signals upon receipt of the ultrasonic waves; and
 a blood flow measuring instrument configured to process the electric signals from the blood flow sensor and to convert the electric signals into a value representing the blood flow rate,
 wherein the blood flow sensor comprises:
  a reflector configured to reflect the generated ultrasonic waves, the reflector being placed on an outer periphery of the blood vessel of the test body;
  a first transducer configured to transmit first ultrasonic waves from a side of the blood vessel opposite to the reflector toward the reflector and to receive second ultrasonic waves reflected by the reflector with the blood vessel of the test body being clamped between the reflector and the first transducer; and
  a second transducer positioned adjacent to the first transducer and on the side of the blood vessel opposite to the reflector, the second transducer being configured to transmit the second ultrasonic waves to be reflected by the reflector toward the first transducer and to receive the first ultrasonic waves reflected by the reflector and transmitted by the first transducer with the blood vessel of the test body being clamped between the reflector and the second transducer,
 wherein the reflector is configured to be changed in distance from the first and second transducers in accordance with a thickness of the blood vessel to be clamped between the first and second transducers and the reflector, and
 wherein the first and second transducers have an angle changing mechanism configured to change an ultrasonic wave transmission/reception angle according to a distance from the reflector so that the ultrasonic waves transmitted by one of the first or second transducer are reflected by the reflector and received by the other of the second or the first transducer despite the change in distance from the reflector.

2. A blood flow measuring instrument including the blood flow probe according to claim 1, wherein the blood flow measuring instrument is configured to include an exterior that can withstand a predetermined sterilization process, the exterior having at least one of airtightness and watertightness that can withstand the predetermined sterilization.

3. The blood flow probe according to claim 1, wherein the blood flow probe includes a sterilization bag configured to cover the blood flow measuring instrument while the blood flow sensor and the blood flow measuring instrument are connected to each other.

4. The blood flow probe according to claim 1, wherein the blood flow sensor and the blood flow measuring instrument are connected via an extension cable configured to maintain an electrically connected state while the blood flow sensor and the blood flow measuring instrument are physically separated from each other.

5. A flow probe, comprising:
 a transmitter positioned on a first side of an outer peripheral surface of a tubular structure, the transmitter being configured to transmit an ultrasonic wave through the tubular structure;
 a receiver configured to receive the ultrasonic wave transmitted through the tubular structure; and
 an angle changing mechanism configured to change a relative angle between the outer peripheral surface of the tubular structure and the transmitter and/or receiver based on a diameter of the tubular structure.

6. The flow probe according to claim 5, wherein the angle changing mechanism is configured to change the relative angle between the outer peripheral surface of the tubular structure and both the transmitter and the receiver.

7. The flow probe according to claim 5, wherein the angle changing mechanism is configured to change a relative angle between the transmitter and the receiver.

8. The flow probe according to claim 5, further comprising a reflector, wherein:
 the reflector is positioned on a second side of the outer peripheral surface of the tubular structure, the second side being opposite the first side of the outer peripheral surface, and the reflector is configured to reflect the ultrasonic wave transmitted by the transmitter toward the receiver.

9. The flow probe according to claim 8, wherein a relative angle between the reflector and the outer peripheral surface is configured to be constant as the relative angle between the outer peripheral surface of the tubular structure and the transmitter and/or receiver is changed based on the diameter of the tubular structure.

10. The flow probe according to claim 9, wherein the tubular structure is a blood vessel.

11. A blood flow probe, comprising:
a transmitter configured to be positioned on a first side of a blood vessel and to transmit an ultrasonic wave through the blood vessel;
a receiver configured to be positioned on the first side of the blood vessel and to be adjacent to the transmitter, the receiver being configured to receive the ultrasonic wave transmitted through the blood vessel;
a reflector configured to be positioned on a second side of the blood vessel, the second side being opposite the first side of the blood vessel, and configured to reflect the ultrasonic wave transmitted from the transmitter toward the receiver; and
an angle changing mechanism configured to change a relative angle between the transmitter and receiver as a distance between the reflector and the transmitter and/or receiver changes.

12. The blood flow probe according to claim 11, wherein the angle changing mechanism is configured to change a relative angle between the reflector and the transmitter and/or receiver.

13. The blood flow probe according to claim 11, wherein the reflector is configured to reflect the ultrasonic wave from the transmitter to the receiver despite a change in the distance between the reflector and the transmitter and/or receiver.

14. The blood flow probe according to claim 11, wherein:
the transmitter is a first transceiver configured to transmit a first ultrasonic wave and receive a second ultrasonic wave,
the receiver is a second transceiver configured to transmit the second ultrasonic wave and receive the first ultrasonic wave,
the reflector is configured to reflect the first ultrasonic wave from the first transceiver toward the second transceiver, and
the reflector is configured to reflect the second ultrasonic wave from the second transceiver toward the first transceiver.

15. The blood flow probe according to claim 14, wherein a blood flow measuring instrument is configured to measure a blood flow rate through the blood vessel base on a difference in transmission time between the first ultrasonic wave and the second ultrasonic wave.

16. The blood flow probe according to claim 15, wherein the angle changing mechanism is configured to directly contact the transmitter and the receiver.

* * * * *